(12) United States Patent
Lee et al.

(10) Patent No.: US 11,654,449 B2
(45) Date of Patent: May 23, 2023

(54) DEVICE FOR SUPPLYING MIST OF LIQUID AND ASSEMBLY INCLUDING THE SAME

(71) Applicant: L'OREAL, Paris (FR)

(72) Inventors: Chin Kai Lee, Kawasaki (JP); Woo Ram Park, Kawasaki (JP); Vishal Sharma, Kawasaki (JP); Di Chen, Shanghai (CN)

(73) Assignee: L'Oreal, Paris (FR)

( * ) Notice: Subject to any disclaimer, the term of this patent is extended or adjusted under 35 U.S.C. 154(b) by 62 days.

(21) Appl. No.: 17/255,141

(22) PCT Filed: Jun. 21, 2019

(86) PCT No.: PCT/JP2019/025996
§ 371 (c)(1),
(2) Date: Dec. 22, 2020

(87) PCT Pub. No.: WO2020/004664
PCT Pub. Date: Jan. 2, 2020

(65) Prior Publication Data
US 2021/0268533 A1    Sep. 2, 2021

(30) Foreign Application Priority Data

Jun. 29, 2018  (JP) .............................. JP2018-124352

(51) Int. Cl.
*B05B 17/06*    (2006.01)
*B05B 17/00*    (2006.01)

(52) U.S. Cl.
CPC ...... *B05B 17/0653* (2013.01); *B05B 17/0646* (2013.01)

(58) Field of Classification Search
CPC ..... B05B 12/08; B05B 12/081; B05B 1/3006; B05B 14/00; B05B 7/0012;
(Continued)

(56) References Cited

U.S. PATENT DOCUMENTS 5,078,305 A     1/1992  Glynn et al.
5,310,112 A  *  5/1994  Meshberg ......... B05B 11/00442
                                                222/212
(Continued)

FOREIGN PATENT DOCUMENTS

CN     1133584 A    10/1996
CN     1960777 A     5/2007
(Continued)

OTHER PUBLICATIONS

First Office Action dated Feb. 16, 2022, issued in related Chinese Application No. 201980038671.8, filed Jun. 21, 2019, 10 pages.
(Continued)

*Primary Examiner* — Christopher R Dandridge
(74) *Attorney, Agent, or Firm* — Christensen O'Connor Johnson Kindness PLLC

(57) ABSTRACT

The present invention relates to a device (10) for supplying a mist of liquid (F). The device (10) is used in combination with a container (20) with an opening (200) for containing the liquid (F). The device (10) includes a main body (100) comprising: (i) a center axis (C); (ii) a liquid chamber (110) formed inside the main body (100), into which a predetermined amount of liquid (F) can be taken up; (iii) a first port (112) formed in a base wall (114) of the main body (100) forming a bottom surface (116) of the liquid chamber (110) so as to face the opening (200) when the device (10) and the container (20) are combined with each other, through which the liquid (F) can flow; (iv) a second port (118) formed in the base wall (114) at a position different from the position where the first port (112) is formed so as to face the opening (200) when the device (10) and the container (20) are combined with each other, through which the liquid (F) can flow; and (v) an aperture (120) connected to the liquid
(Continued)

chamber (110), through which a mist of liquid (F) can be released to the outside of the main body (100). The device (10) further includes: a connecting section (122) provided on the main body (100) so as to extend from it in a direction away from the base wall (114) and used for connecting the container (20) to the main body (100); an atomizing element (124) interposed between the liquid chamber (110) and the aperture (120) to atomize the liquid (F) taken up in the liquid chamber (110) and release a mist of the liquid (F) to the outside of the main body (100) from the aperture (120); a first valve (126) mounted on the main body (100) corresponding to the first port (112), wherein the first valve (126) permits the liquid (F) in the container (20) flowing into the liquid chamber (110) through the first port (112) under the influence of gravity, and prevents the liquid (F) in the liquid chamber (110) flowing into the container (20) under the influence of gravity; and a second valve (128) mounted on the main body (100) corresponding to the second port (118), wherein the second valve (128) prevents the liquid (F) in the container (20) from flowing into the liquid chamber (110) through the second port (118) under the influence of gravity, and selectively permits or prevents the liquid (F) in the liquid chamber (110) flowing into the container (20) through the second port (118) under the influence of gravity.

8 Claims, 5 Drawing Sheets

(58) Field of Classification Search
CPC ............ B05B 17/0646; B05B 17/0643; A61M 16/209; A61M 16/208; A61M 15/0085; A61M 15/0013; A61M 11/00; A61M 11/005

USPC ........................................................ 239/338
See application file for complete search history.

(56) References Cited

U.S. PATENT DOCUMENTS

| | | | |
|---|---|---|---|
| 2007/0262042 A1* | 11/2007 | Pareja | B65D 49/04 |
| | | | 215/17 |
| 2014/0102584 A1 | 4/2014 | Lasnier et al. | |
| 2014/0166776 A1 | 6/2014 | Fang et al. | |
| 2014/0216443 A1 | 8/2014 | Hu | |
| 2014/0250576 A1* | 9/2014 | Pasquini | B05B 17/0669 |
| | | | 4/223 |
| 2018/0036754 A1 | 2/2018 | Scott et al. | |

FOREIGN PATENT DOCUMENTS

| | | | | |
|---|---|---|---|---|
| CN | 101820938 A | | 9/2010 | |
| FR | 2813291 | * | 3/2002 | ......... B05B 11/0037 |
| FR | 2813291 A1 | | 3/2002 | |
| GB | 2506459 | * | 2/2014 | .......... A61M 11/005 |
| JP | 2008110228 A | | 5/2008 | |
| JP | 2010006451 A | | 1/2010 | |
| JP | 2014025386 A | | 2/2014 | |
| WO | 2005/051467 A1 | | 6/2005 | |
| WO | 2018/103636 A1 | | 6/2018 | |

OTHER PUBLICATIONS

Notice of Allowance dated Nov. 7, 2022, from JP Application No. 2018-124352, filed Jun. 21, 2019, 5 pages.

International Search Report dated Oct. 18, 2019, issued in corresponding International Application No. PCT/JP2019/025996, filed Jun. 21, 2019, 2 pages.

* cited by examiner

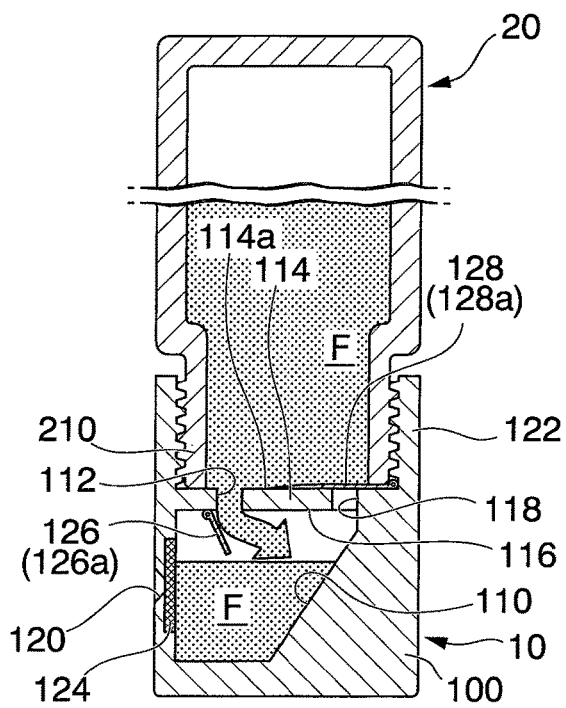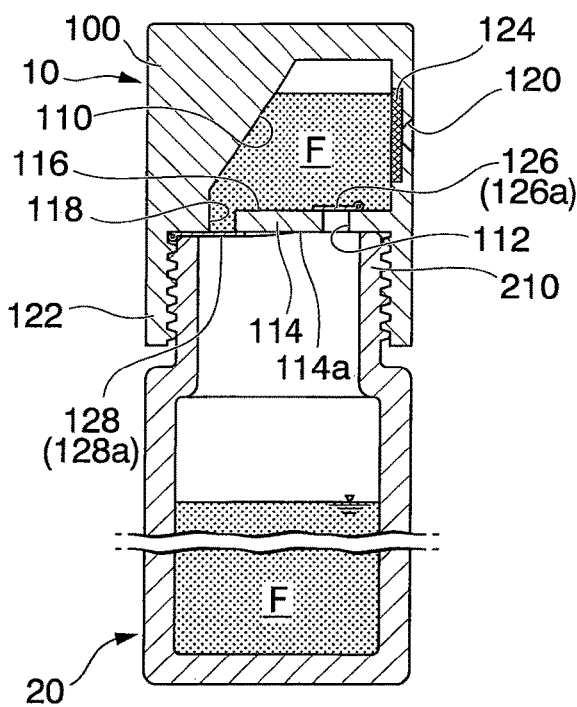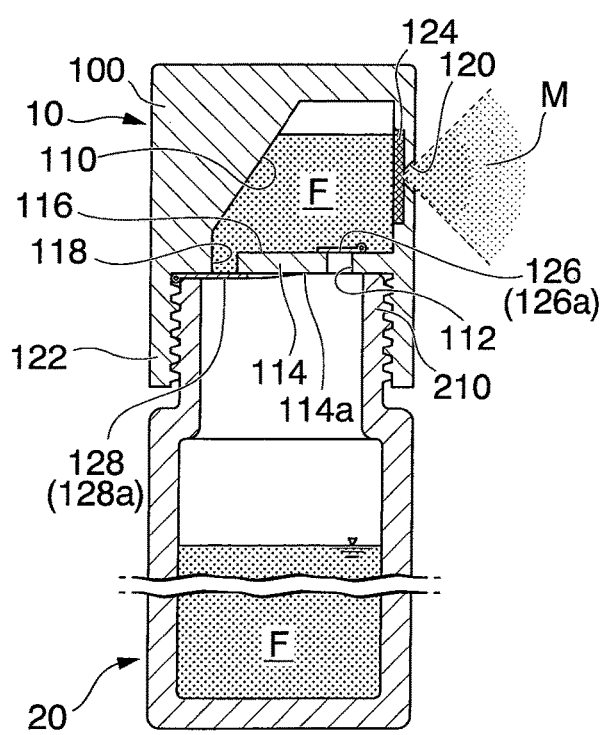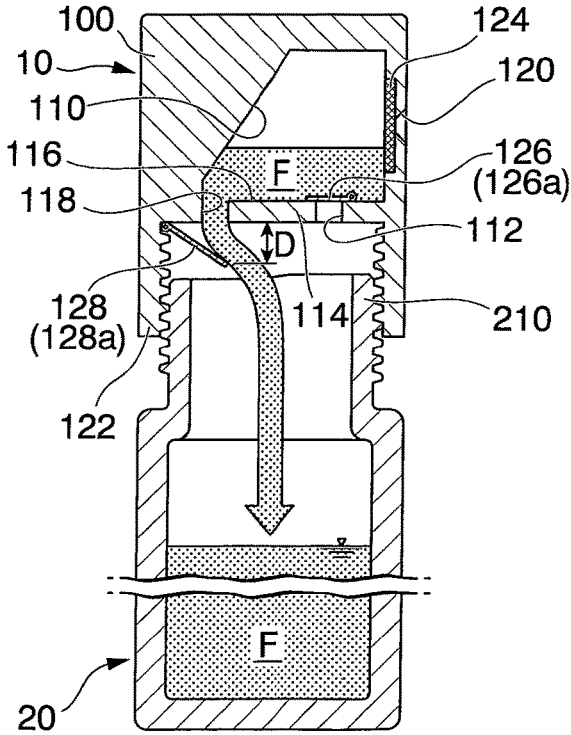

DEVICE FOR SUPPLYING MIST OF LIQUID AND ASSEMBLY INCLUDING THE SAME

TECHNICAL FIELD

The present invention relates to a device for supplying a mist of liquid, for example, water, liquid lotion, liquid medicine or the like. The present invention also relates to an assembly including such a device.

BACKGROUND ART

Currently, compact type ultrasonic devices are widely used to supply liquid such as water as fine mist. These devices can be roughly divided into two types. One is configured so that liquid is supplied to the device from above. This type of device is provided with a liquid reservoir with a lid, and an atomizing element (an ultrasonic vibrating element) for converting a liquid into a mist located adjacent to the reservoir. When the reservoir is empty, the lid is opened and the liquid is supplied to the reservoir. The other is of a type in which a liquid reservoir and an atomizing element are arranged separately in the vertical direction. Such a device is commonly referred to as a "cotton stick type". In this cotton stick type device, an elongated cotton stick is immersed in a liquid in a reservoir, and the liquid is drawn up by capillary action and supplied to the atomizing element that converts the liquid into a mist.

Devices of the type initially described suffer from the following disadvantages. The volume of the reservoir containing the liquid to be released as a mist is generally very small, for example about 5 to 10 ml. Therefore, if the device is continuously used, the reservoir will be emptied in a relatively short time, and it will be necessary to refill the liquid frequently. In order to refill the liquid, it is necessary to open the lid of the reservoir and pour a predetermined amount of liquid carefully from a refill port into the reservoir so as not to spill it, but this is laborious. Furthermore, for this device, it is not easy to enlarge the reservoir since a large-scale design change in the device itself is required for this purpose. In addition, in this existing device, the type of liquid to be released as a mist cannot be easily changed. If the user wishes to change the type of liquid, it is necessary to fully exhaust the liquid already contained in the reservoir.

With regard to the cotton stick type device, refilling the liquid is also laborious work. Furthermore, the cotton stick type device does not allow exchange of the type of liquid to be released as a mist. In the cotton stick type device, liquid which has been used until then penetrates the cotton stick in a large amount. Therefore, when a different kind of new liquid is refilled in the reservoir, the liquid used until then mixes with this new liquid in the cotton stick.

DISCLOSURE OF THE INVENTION

In view of the above, an object of the present invention is to provide a novel device for supplying a mist of liquid and an assembly including such a device. In particular, an object of the present invention is to provide a novel device for supplying a mist of liquid which is capable of easily accommodating changes in the capacity of a liquid reservoir, i.e., a liquid storage unit. A further object of the present invention is to provide a novel device for supplying a mist of liquid which enables easily refilling of a liquid to be released as a mist by a user. A still further object of the present invention is to provide a novel device for supplying a mist of liquid which enables replacing the liquid being used with another kind of liquid without mixing of the two, even before using up the liquid being used.

In order to achieve these objects, the present invention provides a device for supplying a mist of liquid that is intended to be used in combination with a container with an opening for containing the liquid. The device according to the present invention includes a main body comprising: (i) a center axis; (ii) a liquid chamber formed inside the main body, into which a predetermined amount of liquid can be taken up; (iii) a first port formed in a base wall of the main body forming a bottom surface of the liquid chamber so as to face the opening of the container when the device and the container are combined with each other, through which the liquid can flow; (iv) a second port formed in the base wall of the main body at a position different from the position where the first port is formed so as to face the opening of the container when the device and the container are combined with each other, through which the liquid can flow; and (v) an aperture connected to the liquid chamber, through which a mist of liquid can be released to the outside of the main body. The device according to the present invention further comprises: a connecting section provided on the main body so as to extend from the main body in a direction away from the base wall of the main body and used for connecting the container to the main body; an atomizing element interposed between the liquid chamber and the aperture to atomize the liquid taken up in the liquid chamber and release a mist of the liquid to the outside of the main body from the aperture; a first valve mounted on the main body corresponding to the first port, wherein the first valve permits the liquid in the container flowing into the liquid chamber through the first port under the influence of gravity, and prevents the liquid in the liquid chamber flowing into the container under the influence of gravity; and a second valve mounted on the main body corresponding to the second port, wherein the second valve prevents the liquid in the container from flowing into the liquid chamber through the second port under the influence of gravity, and selectively permits or prevents the liquid in the liquid chamber flowing into the container through the second port under the influence of gravity.

According to the present invention, the device for supplying a mist of the liquid is designed not to include the integrated liquid reservoir. Instead, the device according to the present invention is designed to be freely combined with a liquid storage unit, i.e., the container for containing the liquid that can have various capacities, via the connection section. Thus, the device according to the present invention can easily accommodate changes in the capacity of the liquid storage unit (the liquid container) as needed. Furthermore, the device according to the present invention comprises a first valve which permits or blocks the flowing of liquid between the device and the container in response to an orientation of an assembly consisting of the device and the container (for example, an orientation along the vertical line parallel to the direction of gravity), and a second valve which selectively permits or blocks the flow of liquid between the device and the container. Thus, for example, by handling the assembly so that the assembly is first in an inverted state (i.e., the state in which the container is above the device) over a period of time and then in its use state (i.e., the state in which device is above the container), the user can easily refill the liquid in the container into the device. Furthermore, with the configuration stated above, the user can return the liquid being used in the device to the container as needed, even while operating the device. Therefore, according to the present invention, it is possible to easily replace the liquid being used with another kind of liquid without mixing of the two, even before using up the liquid being used.

According to one preferred aspect of the present invention, the atomizing element may be a piezoelectric element, particularly a mesh-shaped piezoelectric element. The piezoelectric element is also called an ultrasonic vibrator and exerts a desired function by being applied with a high frequency alternating or pulsated voltage.

According to one preferred aspect of the present invention, the first valve may comprise a first flap which is disposed within the liquid chamber and which is rotatable around a first flap axis orthogonal or approximately orthogonal to the center axis, wherein the first flap of the first valve blocks the flowing of liquid by being pressed against the bottom surface of the liquid chamber by the weight of the liquid in the liquid chamber.

According to one preferred aspect of the present invention, the second valve may comprise a second flap which is disposed outside the liquid chamber and which is rotatable around a second flap axis orthogonal or approximately orthogonal to the center axis, wherein the second flap of the second valve blocks the flowing of the liquid from the container to the liquid chamber by being pressed against an outer surface of the base wall of the main body by the weight of the liquid in the container. In this aspect, the second flap may be brought into abutment with the opening-side end of the container approaching the outer surface of the base wall of the main body when the container is connected to the device, and wherein the second flap may block the flowing of the liquid from the liquid chamber to the container and vice versa by being pressed against the outer surface of the base wall of the main body by the opening-side end of the container. This aspect is particularly desirable because it can realize a desired valve function with a simple structure. Furthermore, in this aspect, when the outer surface of the base wall of the main body and the opening-side end of the container are spaced apart from each other in order to detach the container from the device, thereby occurring a clearance between the second flap and the outer surface of the base wall, the second flap may permit the liquid in the liquid chamber to flow into the container through the second port under the influence of gravity. This aspect is also particularly desirable because it can realize a desired valve function with a simple structure.

According to one preferred aspect of the present invention, the connecting section of the device and the opening-side end of the container may be connected by screw-in connection. However, other means such as interference fit may be suitably adopted for connection between the connecting section and the opening-side end of the container.

In addition to the above, the present invention further provides an assembly comprising: the aforementioned device for supplying a mist of liquid, and a container, which is connected to the device, for containing the liquid.

BRIEF DESCRIPTION OF THE DRAWINGS

Non-limiting and representative embodiments of the present invention will now be explained in detail below referring to the attached drawings.

FIG. 4 is a schematic cross-sectional view of the assembly comprising the device and liquid container shown in FIG. 1, showing the situation in which the liquid chamber in the device is filled with liquid, the assembly being turned 180° from the position in FIG. 2.

FIG. 5 is a schematic cross-sectional view of the assembly comprising the device and liquid container shown in FIG. 1, showing the situation in which the filling of liquid into the liquid chamber in the device has been completed, the assembly being turned further 180° from the position of FIG. 4 back to the position of FIG. 2.

FIG. 6 is a schematic cross-sectional view of the assembly comprising the device and liquid container shown in FIG. 1, showing the situation in which the device is operated to release the liquid filled in its liquid chamber.

FIG. 7 is a schematic cross-sectional view of the assembly comprising the device and liquid container shown in FIG. 1, showing the situation in which the liquid in the liquid chamber of the device is being returned into the liquid container, the device being moved upward by a predetermined distance with respect to the liquid container.

DETAILED DESCRIPTION OF EMBODIMENTS

Figure 1:
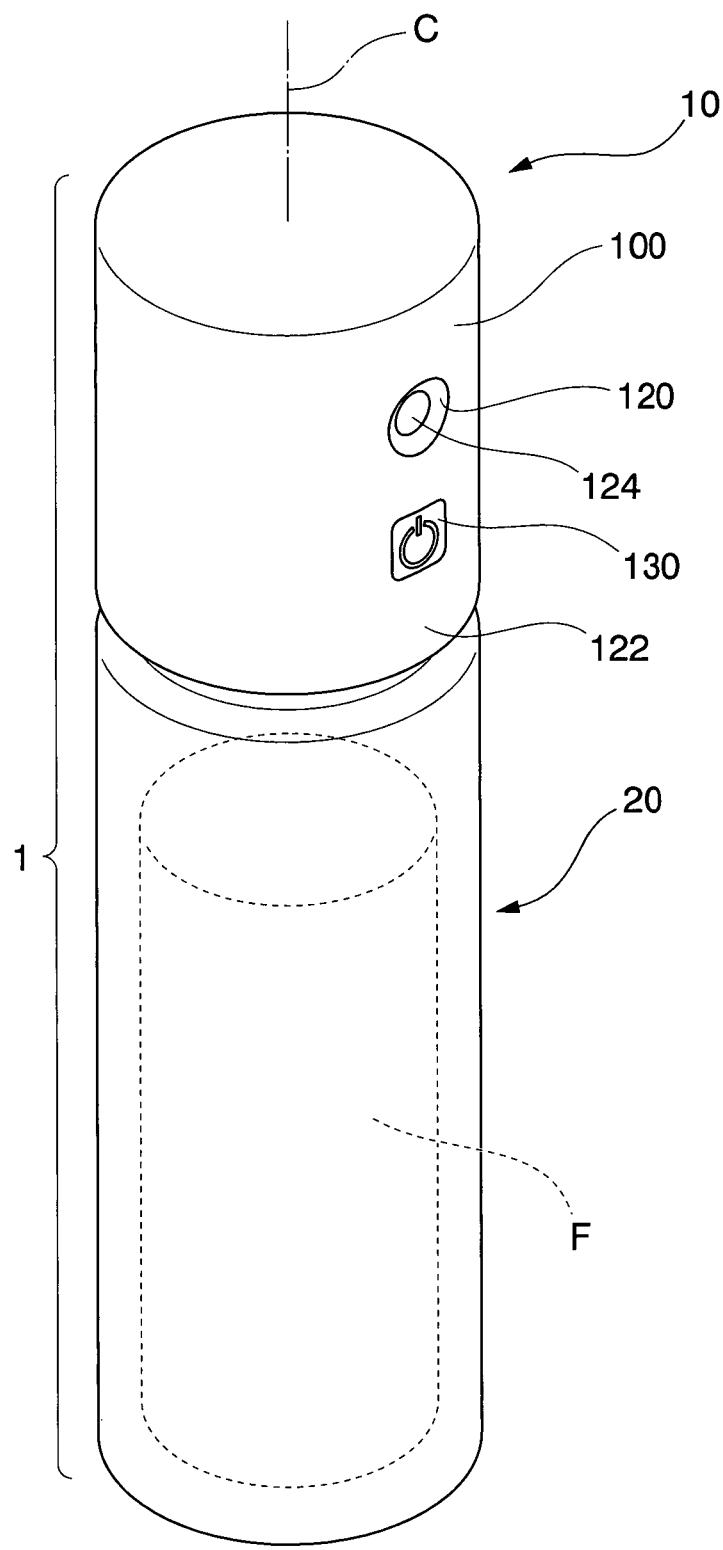
FIG. 1 is a perspective external view of an assembly, in particular a device for supplying a mist of liquid according to an embodiment of the present invention, the device is in a state of being combined with a liquid container.
Figure 2:
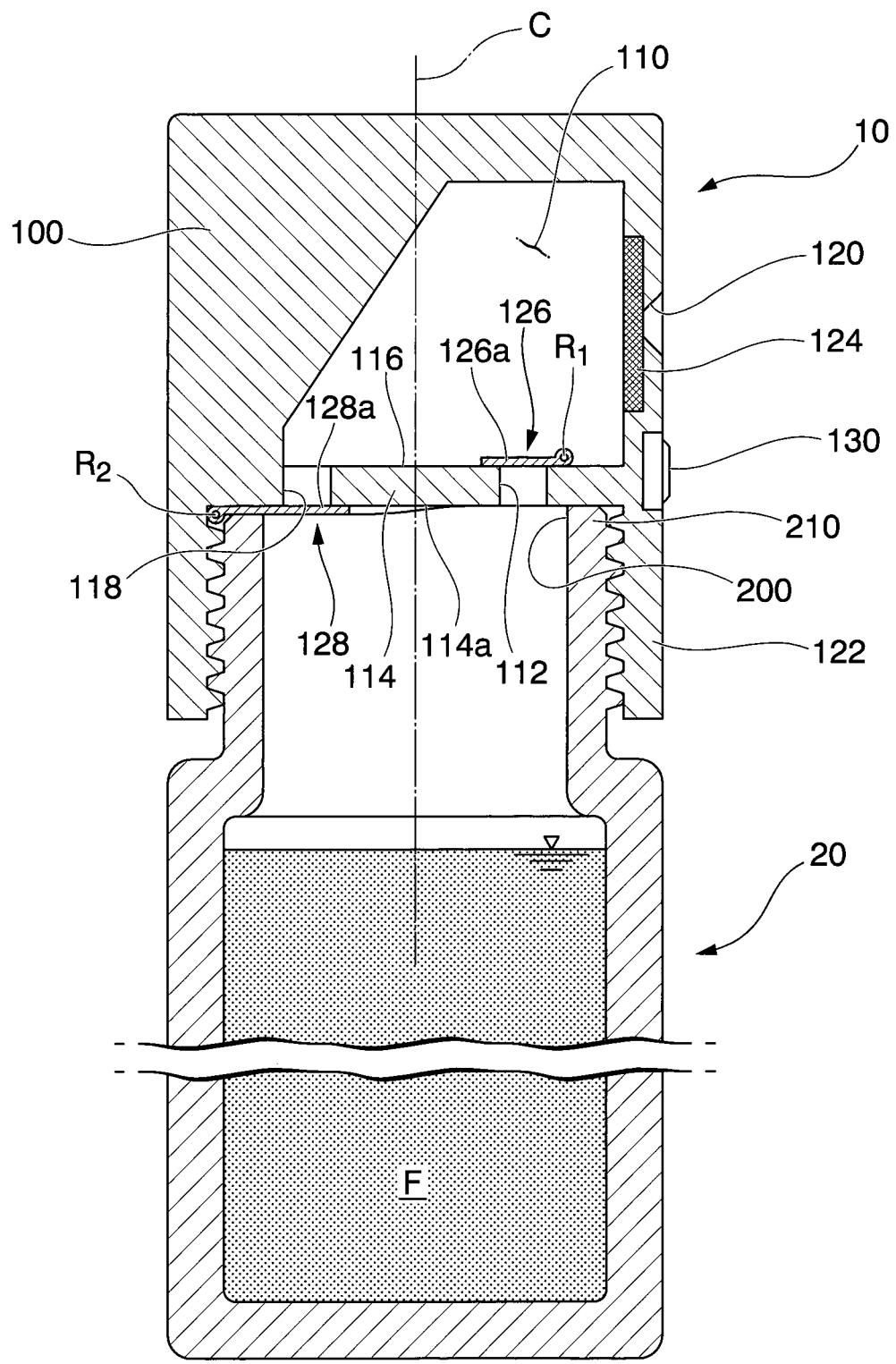
FIG. 2 is a schematic cross-sectional view of the assembly comprising the device and liquid container shown in FIG. 1 through the centerline thereof with a liquid chamber in the device being empty.

An exemplary embodiment of the present invention will now be described with reference to FIGS. 1 to 8. FIG. 1 shows an assembly which is an exemplary embodiment of the present invention. In FIG. 1, this assembly, roughly indicated by a reference numeral 1, includes a device 10 for supplying a mist of liquid, which is also an exemplary embodiment of the invention, and a liquid container 20 as a liquid storage unit combined (connected) with the device 10. In the container 20, the liquid F (for example, water containing cosmetic or medical ingredients) to be released by the action of the device 10 as a mist is contained. The container 20 is made of plastic, glass or the like and has a predetermined internal volume (for example, tens to several hundred ml). The container 20 has an opening 200 and an opening-side end 210 on the upper end thereof as shown in FIG. 2. Furthermore, at the opening-side end 210 of the container 20, a screw thread used for connecting with the device 10 is formed.

As best seen in FIG. 2, the device 10 generally comprises a main body 100, a connecting section 122 extending away from a bottom wall 114 of the main body 100, an atomizing element 124 assembled to the main body 100 to release a mist of the liquid F to the outside of the main body 100, and first and second valves (one-way valves) 126, 128 mounted on the main body 100. The main body 100 may be formed by combining several parts made of plastic, for example. The connecting section 122 is used for connecting the container 20 to the main body 100. In this exemplary embodiment, the main body 100 and the connecting section 122 are integrated together, but they may be separate bodies. In addition, in this embodiment, the connecting section 122 of the device 10 and the opening-side end 210 of the container 20 are connected by a screw-in connection, but other connection system or method may be adopted.

As an example, the main body 100 may have a substantially cylindrical external shape having a center axis C as shown in FIG. 1. The main body 100 has a liquid chamber 110 defined therein, in which a predetermined amount of liquid F can be taken up from the container 20 in a manner detailed below. The main body 100 also includes a first port 112 and a second port 118 through which liquid F can flow. The first port 112 is formed in a base wall 114 of the main body 100 forming a bottom surface 116 of the liquid chamber 110, so as to face the opening 200 of the container 20 when the device 10 and the container 20 are combined with each other. On the other hand, the second port 118 is formed in the base wall 114 of the main body 100 at a position different from the position where the first port 112 is formed. Similarly to the first port 112, the second port 118 faces the opening 200 of the container 20 when the device 10 and the container 20 are combined with each other.

The body 100 further includes an aperture 120 formed through its peripheral wall and connected to the liquid chamber 110. The mist of the liquid F taken up in the liquid chamber 110 can be released to the outside of the main body 100 via the aperture 120. In this exemplary embodiment, the aperture 120 is circular and has a conical shape in the depth direction, but any other configuration of the aperture 120 may be used as required.

Figure 3:
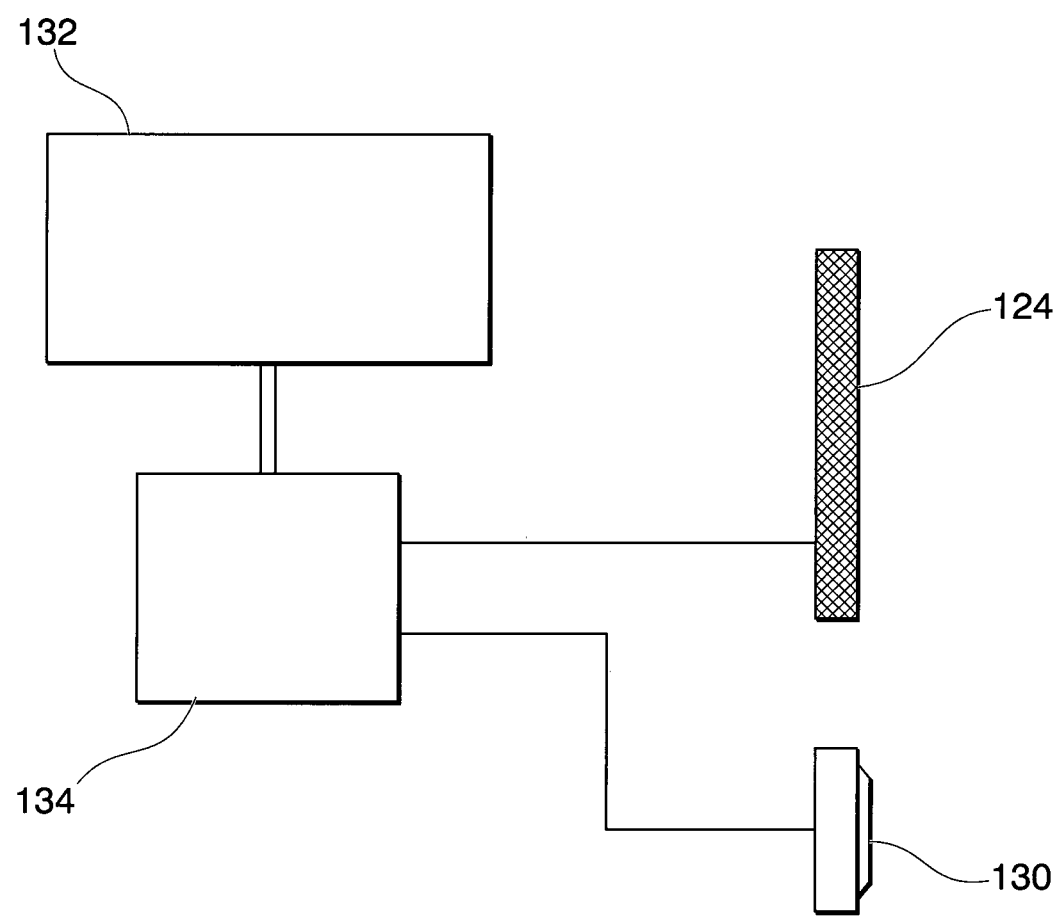
FIG. 3 is a schematic block diagram showing the connection between an atomizing element of the device shown in FIG. 1 and its related components.

Referring again to FIG. 2, the atomizing element 124 is interposed between the liquid chamber 110 and the aperture 120. When a switch 130 mounted on an outer circumferential surface of the main body 100 is turned ON, the atomizing element 124 atomizes the liquid F taken up into the liquid chamber 110 and releases the mist of the liquid F from the aperture 120 to the outside of the main body 100. In this exemplary embodiment, although not limited thereto, the atomizing element 124 is a piezoelectric element commonly referred to as a "piezo mesh". In addition to the atomizing element 124 and the switch 130 stated above, the device 10 further comprises a battery 132 and a drive circuit 134 for the atomizing element 124, which are not shown in FIG. 2 but shown in FIG. 3. The atomizing element 124, the switch 130, the battery 132 and the drive circuit 134 are connected generally as shown in FIG. 3. By turning on the switch 130, high frequency alternating or pulsated voltage is applied to the atomizing element 124 from the drive circuit 134. With the atomizing element 124 driven in this way, the liquid F in the liquid chamber 110 in contact with the atomizing element 124 is atomized into a mist and released from the aperture 120 to the outside of the main body 100.

In this exemplary embodiment, the switch is of the type turning the ON/OFF state by pushing a small boss provided on the outer peripheral surface of the main body 100, but any other type of switch may be used. As an example, a cover piece slidable in the vertical direction along the outer peripheral surface of the main body 100 so as to close/open the aperture 120 for releasing the mist may be used as a switch for activating or stopping the atomizing element 124. In this case, when the cover piece is lowered (or lifted) so as to open the aperture 120, the atomizing element 124 is actuated, whereas when the cover piece is lifted (or lowered) so as to close the aperture 120, the action of the atomizing element 124 stops.

Subsequently, the first and second valves 126, 128 which play a particularly important role in the embodiment of the present invention will be described in detail. As seen in FIG. 2, the first valve 126 is mounted on the main body 100 corresponding to the first port 112 thereof. The first valve 126 permits the liquid F in the container 20 flowing into the liquid chamber 110 through the first port 112 under the influence of gravity (see the state shown in FIG. 4). Furthermore, the first valve 126 prevents the liquid F in the liquid chamber 110 flowing into the container 20 under the influence of gravity (see the states shown in FIGS. 5 to 7). Similarly, the second valve 128 is mounted on the main body 100 corresponding to the second port 118 thereof. The second valve 128 prevents the liquid F in the container 20 from flowing into the liquid chamber 110 through the second port 118 under the influence of gravity (see the state shown in FIG. 4). Furthermore, the second valve 128 selectively permits or prevents the liquid F in the liquid chamber 110 flowing into the container 20 through the second port 118 under the influence of gravity (see the state shown in FIG. 7 and the states shown in FIGS. 5 and 6). In this exemplary embodiment, one first valve and one second valve are mounted on the main body 100. However, if necessary or if space permits, a plurality of first valves and/or second valves may be mounted on the main body 100 (together with corresponding first ports and/or second ports).

Referring again to FIG. 2, the first valve 126 comprises a first flap 126a which is disposed within the liquid chamber 110 and rotatable around a first flap axis $R_1$ orthogonal (or approximately orthogonal) to the center axis C. The first flap 126a of the first valve 126, as stated above, blocks the flowing of liquid F by being pressed against the bottom surface 116 of the liquid chamber 110 by the weight of the liquid F in the liquid chamber 110. The first flap 126a functions in this way, for example, when the assembly 1 is in the upright state as shown in FIGS. 5 to 7 (i.e., the state in which the device 10 is located above the container 20).

The second valve 128 also comprises a second flap 128a which is disposed outside the liquid chamber 110 and which is rotatable around a second flap axis $R_2$ orthogonal (or approximately orthogonal) to the center axis C. The second flap 128a of the second valve 128, as stated above, is capable of blocking the flowing of the liquid F from the container 20 to the liquid chamber 110 by being pressed against the outer surface 114a of the base wall 114 of the main body 100 by the weight of the liquid F in the container 20. The second flap 128a functions in this way, for example, when the assembly 1 is in the inverted state as shown in FIG. 4 (i.e., a state in which the device 10 is positioned below the container 20). However, this function of the second flap 128a is a redundant function in this embodiment. This is because in this embodiment the pressing of the second flap 128a against the outer surface 114a of the base wall 114 of the main body 100 is made by contact with the opening-side end 210 of the container 20.

More specifically, in this exemplary embodiment, the second flap 128a is brought into abutment with the opening-side end 210 of the container 20 approaching the outer surface 114a of the base wall 114 of the body 100 when the container 20 is connected to the device 10. The second flap 128a, as stated above, blocks the flowing of the liquid F from the liquid chamber 110 to the container 20 by being pressed against the outer surface 114a of the base wall 114 of the main body 100 by the opening-side end 210 of the container 20. Unlike the first flap 126a, this blocking function of the second flap 128a is maintained irrespective of the attitude of the assembly 1 once the device 10 and the container 20 are fully combined. The technique for locking the second flap 128a by the opening-side end 210 of the container 20 as described herein is particularly preferred because the structure for realizing it is simple and reliable. However, any other mechanisms for locking the second flap 128a may be additionally or alternately provided on the device.

Furthermore, the second flap 128a becomes freely rotatable downward when the outer surface 114a of the base wall 114 of the main body 100 and the opening-side end 210 of the container 20 are spaced apart from each other in order to detach the container 20 from the device 10. As a result, a clearance D for passing the liquid F can occur between the second flap 128a and the outer surface 114a of the base wall 114 (see FIG. 7). In this way, the second flap 128a, as stated above, permits the liquid F in the liquid chamber 110 to flow into the container 20 through the second port 118 under the influence of gravity. The second flap 128a functions in this way, for example, when the assembly 1 is in an upright state as shown in FIG. 7 (that is, the state in which the device 10 is positioned above the container 20).

Hereinafter, the operation of the device 10 configured as described above and the method for using the assembly 1 containing the liquid F will be described with reference to FIGS. 4 to 8 (assuming that initially the liquid chamber is empty). For the sake of clarity, in FIGS. 4 to 8, it should be noted that the above described switches and the like are omitted.

Prior to the supply of the mist of the liquid F, firstly, the orientation of the assembly 1 is inverted about 180° as shown in FIG. 4. Then, the first flap 126a of the first valve 126 pivots downward due to the weight of the liquid F in the container 20, and the first port 112 opens, so that the liquid F in the container 20 flows into the liquid chamber 110. Meanwhile, the second flap 128a of the second valve 128 remains closed, blocking the flowing of liquid F from the container 20 to the liquid chamber 110.

After a predetermined amount of liquid F has been taken up into the liquid chamber 110 in this way, the assembly 1 is returned again to the upright state as shown in FIG. 5, that is, the state where the device 10 is positioned above the container 20. In this state, the second flap 128a of the second valve 128 still remains closed, while the first flap 126a of the first valve 126 blocks the flowing of the liquid F by being pressed against the bottom surface 116 of the liquid chamber 110 by the weight of the liquid F in the liquid chamber 110.

After reaching the state shown in FIG. 5, when the switch 130 is turned ON, the atomizing element 124 is operated, and as a result, the liquid F in the liquid chamber 110 is released from the aperture 120 to the outside of the device 10 as a mist M as shown in FIG. 6. When the remaining amount in the liquid chamber 110 decreases as a result of operating the device 10 for a certain amount of time, it is necessary to refill the liquid chamber 110. According to the embodiment of the present invention, in this case, the user only need to invert the assembly 1 about 180° to the state shown in FIG. 4, which greatly reduces the effort to refill the liquid F into the liquid chamber 110 compared to conventional devices.

Next, if the user desires to change the type of liquid despite the liquid F remaining in the liquid chamber 110, it is necessary to return the remaining liquid F to the container 20, and subsequently, to replace this container 20 being used with other container containing other kind of liquid. According to the embodiment of the present invention, in this case, the liquid F remaining in the liquid chamber 110 can be returned very easily to the container 20. This is because, as stated above, when the outer surface 114a of the base wall 114 of the main body 100 and the opening-side end 210 of the container 20 are spaced apart from each other in order to detach the container 20 from the device 1, thereby occurring a clearance D between the second flap 128a and the outer surface 114a of the base wall 114, the second flap 128a permits the liquid F in the liquid chamber 110 to flow into the container 20 through the second port 118 under the influence of gravity.

Figure 8:
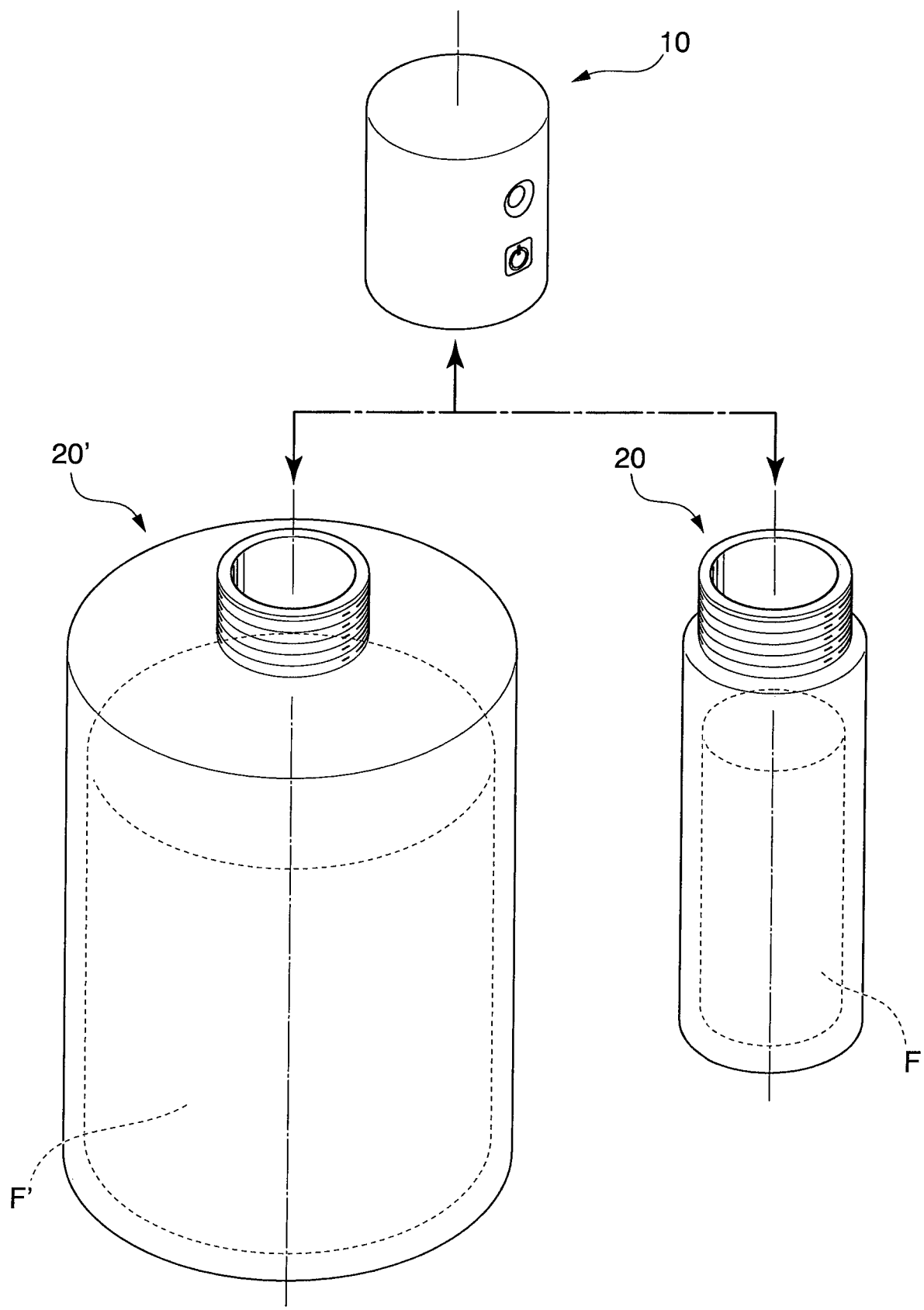
FIG. 8 is a schematic view showing the replacement of the liquid container.

In this way, once the liquid chamber 110 of the device 10 is emptied, the user can replace the container 20 that he/she was using with another container 20' containing another kind of liquid F', for example, a container with a larger capacity, as shown in FIG. 8. Even in this case, since the liquid chamber 110 of the device 10 is once completely emptied, different types of liquids will not mix with each other. Furthermore, according to the embodiment of the present invention configured as described above, it is even possible to replace the container while operating the device. Thus, the device according the embodiment of the present invention can be referred to as a "hot swap" type device.

The preferred embodiments of the present invention have been explained above referring to the drawings. However, the present invention is not limited to these embodiments, and various modifications and changes may be made to the above described embodiments without deviating from the scope of the present invention, and such modifications and changes are also included in the scope of the present invention.

The invention claimed is:

1. A device (10) for supplying a mist of a liquid (F), the device (10) intended to be used in combination with a container (20) with an opening (200) for containing the liquid (F), the device (10) comprising:
a main body (100), the main body (100) comprising:
a center axis (C);
a liquid chamber (110) formed inside the main body (100), into which a predetermined amount of the liquid (F) can be taken up;
a first port (112) formed in a base wall (114) of the main body (100) forming a bottom surface (116) of the liquid chamber (110) so as to face the opening (200) of the container (20) when the device (10) and the container (20) are combined with each other, through which the liquid (F) can flow;
a second port (118) formed in the base wall (114) of the main body (100) at a position different from a position where the first port (112) is formed so as to face the opening (200) of the container (20) when the device (10) and the container (20) are combined with each other, through which the liquid (F) can flow;
an aperture (120) connected to the liquid chamber (110), through which a mist of liquid (F) can be released to the outside of the main body (100);
a connecting section (122) provided on the main body (100) so as to extend from the main body (100) in a direction away from the base wall (114) of the main body (100) and used for connecting the container (20) to the main body (100);
an atomizing element (124) interposed between the liquid chamber (110) and the aperture (120) to atomize the liquid (F) taken up in the liquid chamber (110) and release a mist of the liquid (F) to the outside of the main body (100) from the aperture (120);
a first valve (126) mounted on the main body (100) corresponding to the first port (112), wherein the first valve (126) permits the liquid (F) in the container (20) flowing into the liquid chamber (110) through the first port (112) under the influence of gravity, and prevents the liquid (F) in the liquid chamber (110) flowing into the container (20) under the influence of gravity; and
a second valve (128) mounted on the main body (100) corresponding to the second port (118), wherein the second valve (128) prevents the liquid (F) in the container (20) flowing into the liquid chamber (110) through the second port (118) under the influence of gravity, and selectively permits or prevents the liquid (F) in the liquid chamber (110) flowing into the container (20) through the second port (118) under the influence of gravity.

2. The device (10) according to claim 1, wherein the atomizing element (124) is a piezoelectric element.

3. The device (10) according to claim 1, wherein the first valve (126) comprises a first flap (126a) which is disposed within the liquid chamber (110) and which is rotatable around a first flap axis (R1) orthogonal or approximately orthogonal to the center axis (C), wherein the first flap (126a) of the first valve (126) blocks the flowing of liquid (F) by being pressed against the bottom surface (116) of the liquid chamber (110) by the weight of the liquid (F) in the liquid chamber (110).

4. The device (10) according to claim 1, wherein the second valve (128) comprises a second flap (128a) which is disposed outside the liquid chamber (110) and which is rotatable around a second flap axis ($R_2$) orthogonal or approximately orthogonal to the center axis (C), wherein the second flap (128a) of the second valve (128) blocks the flowing of the liquid (F) from the container (20) to the liquid chamber (110) by being pressed against an outer surface (114a) of the base wall (114) of the main body (100) by the weight of the liquid (F) in the container (20).

5. The device (10) according to claim 4, wherein the second flap (128a) is brought into abutment with an opening-side end (210) of the container (20) approaching the outer surface (114a) of the base wall (114) of the main body (100) when the container (20) is connected to the device (10), and wherein the second flap (128a) blocks the flowing of the liquid (F) from the liquid chamber (110) to the container (20) and vice versa by being pressed against the outer surface (114a) of the base wall (114) of the main body (100) by the opening-side end (210) of the container (20).

6. The device (10) according to claim 5, wherein when the outer surface (114a) of the base wall (114) of the main body (100) and the opening-side end (210) of the container (20) are spaced apart from each other in order to detach the container (20) from the device (10), thereby occurring a clearance (D) between the second flap (128a) and the outer surface (114a) of the base wall (114), the second flap (128a) permits the liquid (F) in the liquid chamber (110) to flow into the container (20) through the second port (118) under the influence of gravity.

7. The device (10) according to claim 1, wherein the connecting section (122) of the device (10) and the opening-side end (210) of the container (20) are connected by screw-in connection.

8. An assembly (1) comprising:
a device (10) for supplying a mist of a liquid (F) according to claim 1; and
a container (20), which is connected to the device (10), for containing the liquid (F).

* * * * *